United States Patent [19]

Frantsits

[11] 4,118,395
[45] Oct. 3, 1978

[54] METHOD FOR THE PRODUCTION OF INDOLYL LACTONES

[76] Inventor: Werner J. Frantsits, Boltzmanngasse 9a-11, Vienna 9, Austria

[21] Appl. No.: 808,272

[22] Filed: Jun. 20, 1977

[30] Foreign Application Priority Data

Jun. 28, 1976 [AT] Austria .............................. 54719/76

[51] Int. Cl.² .......................................... C07D 491/04
[52] U.S. Cl. ...................... 260/326.29; 260/326.13 C
[58] Field of Search ................................. 260/326.29

[56] References Cited

U.S. PATENT DOCUMENTS 3,997,558  12/1976  Frantsits ................. 260/326.13 A

OTHER PUBLICATIONS

Eiter et al.; Mh. Chem. vol. 83, pp. 1453–1476, (1952).
Piper et al.; J. Het. Chem. vol. 3, pp. 95–97, (1966).
Badger et al.; J. Chem. Soc. pp. 1179–1184, (1958).
Plieninger et al.; Ber. vol. 90, pp. 1984–1987, (1957).
Taylor; Helo. Chem. Acta, vol. 33, pp. 164–169, (1950).

Primary Examiner—Donald G. Daus
Assistant Examiner—Mary C. Vaughn
Attorney, Agent, or Firm—Martin A. Farber

[57] ABSTRACT

A method for the production of indolyl lactones of the formula

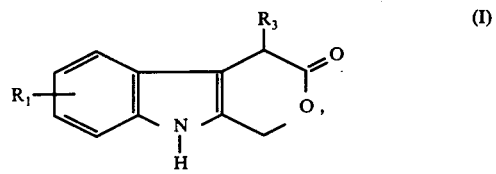

wherein $R_1$ is hydrogen, halogen, or an alkoxy group having 1 to 4 C atoms and $R_3$ is hydrogen, characterized in the manner that one reacts a 2-hydroxymethylindole of the formula

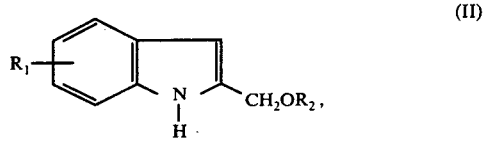

wherein $R_1$ has the above named meaning and $R_2$ is an alkanoyl group or a phenyl alkanoyl group, with an α-diazoester of the formula

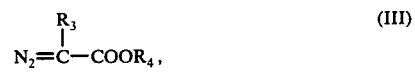

wherein $R_3$ has the above named meaning and $R_4$ is an alkyl group having 1 to 4 C atoms and a, benzyl group, to a 3-indolyl acetic acid ester of the formula

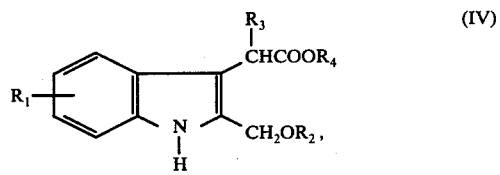

wherein $R_1$, $R_2$, $R_3$ and $R_4$ have the above named meanings, saponifies the thus obtained 3-indolyl acetic acid ester of the formula (IV) to the 3-indolyl acetic acid of the formula

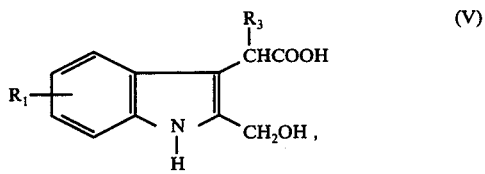

wherein $R_1$ and $R_3$ have the above named meaning, and the latter is dehydrated to indolyl lactone with the formula (I).

7 Claims, No Drawings

METHOD FOR THE PRODUCTION OF INDOLYL LACTONES

The invention relates to a method for the production of δ-valerolactones of the following formula corresponding to 2-hydroxymethyl-3-indolyl acetic acids

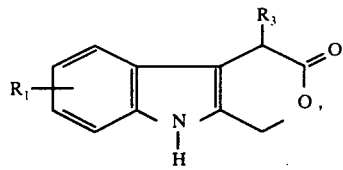 (I)

wherein $R_1$ is hydrogen, halogen, or an alkoxy group having 1 to 4 carbon atoms and $R_3$ is hydrogen.

For the production of this lactone (I) up to now only a method has been known which comprises a cyclization of arylhydrazones of the 4-oxo-δ-valerolactone under the conditions of the Fischer indole synthesis. This method however often produces with respect to the relative instability of the primary formed hydroxymethylindoles compared to the acid agents unfavorable results and results which are difficult to reproduce.

In accordance with the method of the invention one reacts a 2-hydroxymethylindole of the formula

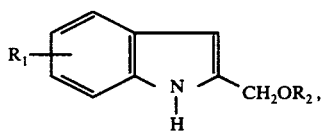 (II)

wherein $R_1$ has the above mentioned meaning and $R_2$ represents an alkanoyl group or a phenyl alkanoyl group, with an α-diazoester of the formula

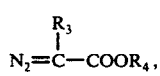 (III)

wherein $R_3$ has the above meaning and $R_4$ is an alkyl group having 1 to 4 carbon atoms and a benzyl group, to a 3-indolyl acetic acid ester of the formula

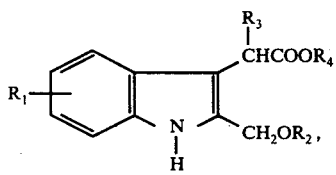 (IV)

wherein $R_1$, $R_2$, $R_3$ and $R_4$ have the above mentioned meanings, saponifies the thus obtained 3-indolyl acetic acid ester of the formula (4) to the 3-indolyl acetic acid of the formula

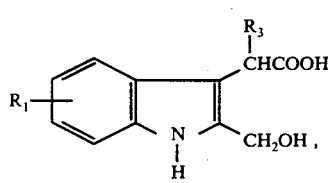 (V)

wherein $R_1$ and $R_3$ have the above named meaning, and dehydrates the latter to the indolyl lactone of the formula (1).

Preferred examples for the group $R_2$ are the acetyl-group or the α-phenylacetyl group.

Advantageously one reacts the 2-hydroxymethylindole of the formula (II) with the α-diazoester of the formula (III) in the presence of a catalyst, preferably under heating, whereby one preferably uses a metal as a catalyst, for example, copper-sponge.

It has proven particularly favorable if one saponifies the 3-indolyl acetic acid ester of the formula (IV) in the presence of an acid to the 3-indolyl acetic acid of the formula (V).

Preferable in accordance with the method of the invention, the 3-indolyl acetic acid of the formula (V) in the presence of a dehydrating agent is dehydrated to indolyl lactone of the formula (I), whereby one advantageously uses an acid anhydride as a dehydrating agent, for example acetic anhydride or dicyclohexylcarbodiimide.

The lactone produced in accordance with the invention, the structure of which was confirmed by reception of mass spectrograms, allows the hydrolysis (outside of the framework of the present invention) in a protein or aprotein solvent with hydrogen in the presence of a noble metal catalyst, preferably palladium on coal, hydrogenolytically to 2-methylindolyl acetic acids of the formula

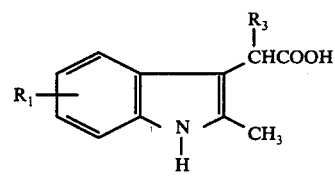

The compounds produced in accordance with the present invention are thus valuable intermediate products for the production of indolyl-3-alkane acid derivatives, which are pharmaceutically interesting compounds. Thus, for example 1-(p-chlorobenzoyl)-2-methyl-5-methoxyindolyl-3-acetic acid (Indomethacin) of the formula

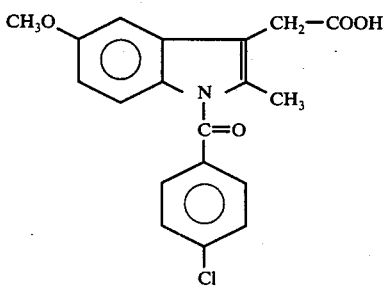

likewise outside of the framework of the present invention can be produced from the corresponding lactone of the formula

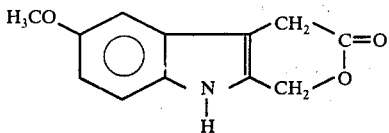

by p-chlorobenzoylating and succeeding hydrogenolytically opening the lactone rings with very good yield.

The intermediate products of the formulae (IV) and (V) occurring by the method in accordance with the present invention are new compounds, the structures of which were verified by reception of nuclear resonance spectra.

Reactions of the diazoacetic esters with unsubstituted indole and 1-alkylindoles, respectively, to the corresponding 3-indolyl acetic acid esters is found in: G. M. Badjer, B. J. Christie, H. J. Rodda and J. M. Pryke, J. Chem. Soc. 1958, 1179; K. Eiter and O. Svierak, Mh. Chem. 83, 1453 (1952); J. R. Piper and F. J. Stevens, J. Heterocyclic Chem. 3, 95 (1966); H. Plieninger and K. Suhr, Ber. 90, 1984 (1957).

The synthesis of the 2-acetoxymethylindole, which starting product is of the set forth example, is described by W. I. Taylor, Helv. 33, 164 (1950).

The invention is more closely explained from the following examples, in which also the production of the starting compound is described:

EXAMPLE 1: Production of the α-valerolactone of the 2-hydroxymethyl-3-indolyl acetic acid (a) 2-acetoxymethylindole: a solution of 2.0 g (1.36 mMol) 2-hydroxymethylindole in 6 ml absolute pyridine is added with 2 ml acetic anhydride and the homogeneous solution is allowed to stand 24 hours at room temperature. After hydrolysis of the excess acetic anhydride by addition of water is coated over with ether and the organic extract is washed several times with water. After drying over sodium sulfate and evaporation of the solvent in vacuum one obtains 2.2 g (1.16 mMol) (85% of the theoretical) 2-acetoxymethylindole, melting point 112° C (from petroleum ether).

$C_{11}H_{11}NO_2$ (189.2)

NMR(CDCl$_3$): δ = 8.66 (width, 1H, —NH); 7.65 (m 1H, H to C-7); 7.24 (m, 3H, H to C-4 – C-6); 6.10 ("d", 1H, H to C-3); 5.28 (s, 2H, —CH$_2$O—); 2.10 (s, 3H, —COCH$_3$).

(b) 2-acetoxymethyl-3-indolyl acetic acid ethyl ester: 1 g (5.29 mMol) 2-acetoxymethylindole was dissolved in 2 ml absolute toluene, added with copper-sponge and the mixture was heated on the boiling water bath. To this one drips drop-wise during 1 hour 0.9 g (7.9 mMol) diazoacetic acid ethyl ester in 1 ml absolute toluene. After the cooling it is filtered and the solvent is removed in vacuum. The residue was chromatographed on Al$_2$O$_3$ (benzene, column 3 × 20 cm). First not reacted educt (0.5 g) was elutriated, then the product: 2-acetoxymethyl-3-indolyl acetic acid ethyl ester was elutriated. Yield: 0.4 g (55% of the theoretical, related to reacted 2-acetoxymethylindole), melting point: 85°-87° C (from petroleum ether).

NMR(acetone-d$_6$): δ = 10.4 (m, 1H, —NH); 8.1 –7.2 (m, 4H, ABCD-system, aromatic protons); 5.55 (s, 2H, —CH$_2$OAc); 4.28 (qu, 2H, —CH$_2$— of the ethyl group); 4.03 (s, 2H, —CH$_2$COOEt); 2.13 (s, 3H, —CO—CH$_3$); 1.27 (t, 3H, —CH$_3$ of the ethyl group).

(c) 2-hydroxymethyl-3-indolyl acetic acid: one dissolved 200 mg (0.73 mMol) 2-acetoxy-3-indolyl acetic acid ethyl ester in 0.5 ml ethanol, added 3 ml 10% aqueous potash lye or caustic potash solution and heated 1 hour on the boiling water bath. The thus obtained solution of the potassium salt was coated over with a layer of ether and with violent stirring was adjusted with diluted phosphoric acid to a pH 5. The aqueous solution was yet still extracted twice with ether and the combined extracts were dried over sodium sulfate. After the evaporation of the solvent in vacuum there remained 130 mg (87% of the theoretical) 2-hydroxymethyl-3-indolyl acetic acid as oil.

(d) Lactone of the 2-hydroxymethyl-3-indolyl acetic acid: the dehydration of the 2-oxymethyl-3-indolyl acetic acid to lactone was undertaken with dicyclohexylcarbodiimide (DCC) in absolute pyridine. For this one dissolved 120 mg (0.58 mMol) 2-hydroxymethyl-3-indolyl acetic acid together with 150 mg (0.73 mMol) DCC in 2 ml pyridine and heated 2 hours at 95° C. After evaporation of the solvent in high vacuum the residue was dissolved in 5 ml methylene chloride, filtered off from the dicyclohexyl urea which arose and thereafter subjected to a preparative thin layer chromatograph (Al$_2$O$_3$, eluant: benzene/ethanol — 100/1). One obtained 98 mg (90% of the theoretical) lactone of the 2-hydroxymethyl-3-indolyl acetic acid, which melted from benzene uncrystallized at 170° C with decomposition.

$C_{11}H_9NO_2$ (187.18).

MS(m/e): 187(65, molecular ion), 185(4), 160(5), 158(5), 149(4), 146(3), 145(4), 144(18), 143(100), 142(20), 140(3), 135(3), 131(13), 130(6), 129(11), 118(6), 117(10), 116(22), 104(8), 103(19), 102(6).

EXAMPLE 2: Production of the lactone of the 2-hydroxymethyl-5-methoxyindolyl acetic acid:

(a) sodium salt of the 4-methoxy-phenylhydrazinesulfonic acid: Lit.: J. Altschul, Ber. 25, 1845 (1892). 100 g p-anisidine was dissolved in 230 ml concentrated hydrochloric acid and 100 ml water (there arose a red crystal precipitate) and at −5° C slowly 61.5 g sodium nitrite in 140 ml water was added drop by drop. After that 264 g sodium hydrogen sulfite was dissolved in 230 ml 30% caustic acid and 1000 ml water, cooled at 5° C and the diazonium salt solution was added. The precipitate (sodium-4-methoxyphenyldiimide sulfonate, yield 190 g) was drawn off, dissolved in 550 ml water as well as 91 ml glacial acetic acid, 25 g powdered zinc was added and gentle heating conducted on the water bath, until the solution decolorized. One then filtered hot and allowed the solution to cool, whereby the sodium-4-methoxyphenylhydrazine sulfonate precipitated. One sucked off the precipitate and dried in the desiccator: yield 145 g.

(b) 5-methoxyindolyl-2-carboxylic acid ethyl ester: 8 g (33.3 mMol) sodium-4-methoxyphenylhydrazine sulfonate was heated together with 3.74 g (32.24 mMol) pyruvic acid ethyl ester and 80 ml absolute ethanolic hydrochloric acid (12% HCl) 30 minutes on the boiling water bath. After the cooling one filtered off from the insoluble materials and poured the filtrate on 250 ml water. After filtration of the precipitate and drying, one obtained 5 g (71% of the theoretical) 5-methoxyindolyl-2-carboxylic ethyl ester, melting point 153°–157° C (from ethanol), $C_{12}H_{13}NO_3$ (MG: 219.24).

MS (m/e): 219(42, molecular ion), 174(21), 173(100), 158 (26), 146(6), 130(11), 119(12), 102(7).

NMR (60 MHz, (CD$_3$)$_2$CO: δ = 10.61 (width, 1H, N—H), 7.41, 7.10, 6.90 (ABC-system, J$_{AB}$ ≃ OHz, J$_{AC}$ = 8Hz, J$_{BC}$ = 2Hz, 3H; H to 3-7, C-4 and C-6), 7.00 (s, 1H; H to C-3), 4.30, 1.35 (A$_2$X$_3$-system, J$_{AX}$ = 7Hz, 5H; ethyl ester group to C-2), 3.80 (s, 3H; O—CH$_3$ to C5).

(c) 2-hydroxymethyl-5-methoxyindole: 1.2 g 5-methoxyindolyl-2-carboxylic acid ethyl ester in 35 ml ether was added with vigorous stirring at 20° C slowly with 0.4 g lithium aluminum hydride. After 1 hour, one carefully decomposed with water and dried the etheric phase over sodium sulfate. After the evaporation of the solvent one obtained 0.7 g (72% of the theoretical) 2-hydroxymethyl-5-methoxyindole, melting point 78°–82° C (from benzene/petroleum ether).

C$_{10}$H$_{11}$NO$_2$ (177.20).

NMR (60 MHz, (CD$_3$)$_2$CO): δ = 9.90 (b, 1H; N—H), 7.23, 6.95, 6.68 (ABC-system, J$_{AB}$ ~ OHz, J$_{AC}$ = 8Hz, J$_{BC}$ = 2 Hz, 3H; H to C-7, C-4 and C-6), 6.21 (s, 1H; H to C-3), 4.69, 4.25 (AX$_2$-system, J$_{AX}$ = 4Hz, 3H; —CH$_2$—OH to C-2), 3.73 (s, 3H; O—CH$_3$ to C-5).

(d) 2-acetoxymethyl-5-methoxyindole: A solution of 1.5 g 2-hydroxymethyl-5-methoxyindole in 6 ml absolute pyridine was added to 2 ml acetic anhydride and the homogeneous solution was allowed to stand 24 hours at 20° C. Thereafter water and ether were added and the organic extract was washed several times with water. After drying over sodium sulfate and evaporation of the solvent in vacuum one obtained 1.65 g (89% of the theoretical) 2-acetoxymethyl-5-methoxyindole, melting point 79°–82° C (from benzene/petroleum ether).

C$_{12}$H$_{13}$NO$_3$ (219.24).

NMR (60 MHz, (CD$_3$)$_2$CO): δ = 9.96 (b, 1H; N—H), 7.32, 7.04, 6.78 (ABC-system, J$_{AB}$ ~ OHz, J$_{AC}$ = 8Hz, J$_{BC}$ = 2Hz, 3H; H to (c-7, C-4 and C-6), 6.44 (s, 1H; H to C-3), 5.23 (s, 2H; CH$_2$—O to C-2), 3.80 (s, 3H; O—CH$_3$ to C-5), 2.00 (s, 3H; COCH$_3$).

(e) 2-acetoxymethyl-5-methoxyindolyl-3-acetic acid ethyl ester: A solution of 1.0 g (4.6 mMol) 2-acetoxymethyl-5-methoxyindole in 2 ml toluene was added with copper-sponge and on the boiling water bath 1 g (8.8 mMol) diazoacetic ester in 1 ml absolute toluene was added dropwise within 1 hour. After the cooling it was filtered, evaporated under vacuum and the residue chromatographed on Al$_2$O$_3$ (benzene, column 3 × 20 cm). Initially one elutriates not reacted educt (0.45 g), and thereafter 2-acetoxymethyl-5-methoxyindolyl-3-acetic acid ethyl ester. Yield 0.41 g (54% of the theoretical, related to reacted educt), melting point 115°–120° C (from benzene/petroleum ether).

C$_{16}$H$_{19}$NO$_5$ (305.32).

MS (m/e): 305(36 molecule ion), 246(38), 245(20), 232(12), 188(13), 174(20), 173(39), 172(100), 160(11), 159(8), 158(27), 145(5), 130(7), 117(5), 116(7), 105(5).

NMR (60MHz, (CD$_3$)$_2$CO): δ = 10.00 (b, 1H; N—H), 7.22, 7.03, 6.72 (ABC-system, J$_{AB}$ ~ OHz, J$_{AC}$ = 8Hz, J$_{BC}$ = 2Hz, 3H; H to C-7, C-4 and C-6), 5.20 (s, 2H; CH$_2$-0 to C-2), 4.05, 1.13 (A$_2$X$_3$-system, J$_{AX}$ = 7Hz, 5H; Ethyl ester group to C-3), 3.78 (s, 3H; O—CH$_3$ to C-5), 2.90 (s, 2H; CH$_2$ to C-3), 2.00 (s, 3H, COCH$_3$).

(f) 2-hydroxymethyl-5-methoxyindolyl-3-acetic acid: The saponification of the ester to 5-methoxy-2-oxymethyl-3-indolyl acetic acid takes place as stated in example 1 (c), whereby one obtains from 818 mg of the ester 634 mg of the hydroxy acid.

(g) Lactone of the 2-hydroxymethyl-5-methoxyindolyl-3-acetic acid: By dehydration of 634 mg of the 2-hydroxymethyl-5-methoxyindolyl-3-acetic acid according to the manner of operation set forth in example 1 (d) one obtains 500 mg lactone, which was uncrystallized from benzene. Melting point 185° C (under decomposition).

C$_{12}$H$_{11}$NO$_3$ (217.24).

MS (m/e): 217 (37, molecular ion). 174(20), 173(78), 172(11), 160(9), 159(15), 158(100), 130(22), 117(9), 116(8), 103(12).

I claim:

1. A method for the production of indolyl lactones of the formula

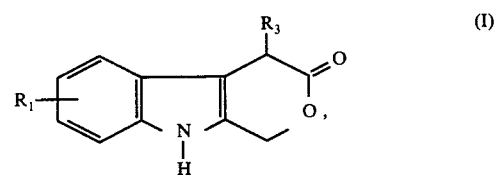

wherein R$_1$ is a member of the group consisting of hydrogen, halogen and an alkoxy group having 1 to 4 C atoms and R$_3$ is hydrogen, comprising the steps of reacting a 2-hydroxymethylindole of the formula

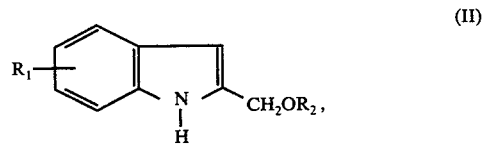

wherein R$_1$ has the above named meaning and R$_2$ is a member of the group consiting of an alkanoyl group and a phenyl alkanoyl group, with an α-diazoester of the formula

wherein R$_3$ has the above named meaning and R$_4$ is an alkyl group having 1 to 4 carbon atoms or a benzyl group, to a 3-indolyl acetic acid ester of the formula

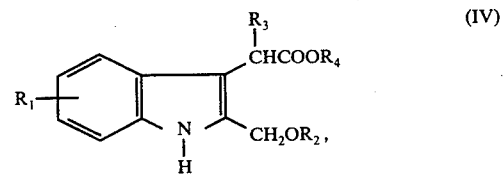

wherein R$_1$, R$_2$, R$_3$ and R$_4$ have the above named meanings, saponifying the thus obtained 3-indolyl acetic acid ester of the formula (IV) to the 3-indolyl acetic acid of the formula

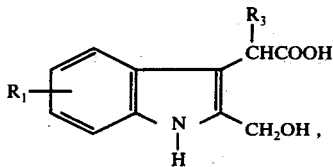 (V)

wherein $R_1$ and $R_3$ have the above named meaning, and dehydrating the latter to indolyl lactone of the formula (I).

2. The method according to claim 1, wherein the step of reacting of the 2-hydroxymethylindole of the general formula (II) with the α-diazoester of the general formula (III) is performed in the presence of a catalyst.

3. The method according to claim 2, wherein the step of reacting is further performed with heating.

4. The method according to claim 2, wherein the catalyst is metal.

5. The method according to claim 4, wherein the catalyst is copper-sponge.

6. The method according to claim 1, further comprising the step of saponifying the 3-indolyl acetic acid ester of the formula (IV) in the presence of an acid to the 3-indolyl acetic acid of the formula (V).

7. The method according to claim 1, wherein the step of dehydrating the 3-indolyl acetic acid of the formula (V) is performed in the presence of a dehydrating agent selected from the group consisting of acetic anhydride and dicyclohexylcarbodiimide to the indolyl lactone of the formula (I).

* * * * *